(12) United States Patent
Yoshida et al.

(10) Patent No.: US 6,531,602 B2
(45) Date of Patent: Mar. 11, 2003

(54) 2-PYRIDYSILANE, PROCESSES FOR PRODUCING AND USING THE SAME

(75) Inventors: Junichi Yoshida, Hirakata (JP); Kenichiro Itami, Kyoto (JP); Seiji Suga, Kyoto (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/140,170

(22) Filed: May 8, 2002

(65) Prior Publication Data

US 2002/0165397 A1 Nov. 7, 2002

Related U.S. Application Data

(62) Division of application No. 09/522,615, filed on Mar. 10, 2000.

(30) Foreign Application Priority Data

Mar. 10, 1999 (JP) ............................................ 11-063215
Mar. 10, 1999 (JP) ............................................ 11-063216

(51) Int. Cl.[7] .............................. C07F 7/10; C07F 7/20
(52) U.S. Cl. ....................................................... 546/14
(58) Field of Search ....................................... 546/14, 1

(56) References Cited

U.S. PATENT DOCUMENTS 4,883,789 A   11/1989  Sieburth
6,416,861 B1 * 7/2002  Lee et al. ................... 428/391

OTHER PUBLICATIONS

Tetrahedron Letters, vol. 40, No. 17 (1999) pp. 3403–3406.
Tetrahedron Letters, vol. 40, No. 30 (1999) pp. 5533–5536.
Tetrahedron Letters, vol. 40 (1999) pp. 5537–5540.
The Journal of Organic Chemistry, vol. 64, No. 23 (1999) pp. 8709–8714.
The Journal of Organic Chemistry, vol. 62, No. 4 (1997) pp. 1112–1124.

* cited by examiner

Primary Examiner—Alan L. Rotman
Assistant Examiner—Rita Desai
(74) Attorney, Agent, or Firm—Birch, Stewart, Kolasch & Birch, LLP

(57) ABSTRACT

The present invention provides a compound which can be purified by conventional acid/base extraction.

There is disclosed 2-pyridylsilane of formula (1):

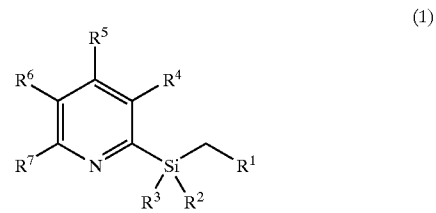

(1)

wherein $R^1$ represents an alkyl group, etc, $R^2$ and $R^3$ represent an alkyl group, an alkoxy group, etc, $R^4$, $R^5$, $R^6$ and $R^7$ represent a hydrogen atom, a halogen atom, an alkyl group, etc.

2 Claims, No Drawings

2-PYRIDYSILANE, PROCESSES FOR PRODUCING AND USING THE SAME

This application is a divisional of co-pending application Ser. No. 09/522,615, filed on Mar. 10, 2000, the entire contents of which are hereby incorporated by reference and for which priority is claimed under 35 U.S.C. §120; and this application claims priority of application Ser. No. 11-063215 and 11-063216 filed in JAPAN on Mar. 10, 1999 under 35 U.S.C. §119.

BACKGROUND OF THE INVENTION

1. Field of the Invention

The present invention relates to novel 2-pyridylsilanes, processes for the same, an intermediates therefor and a process for producing an alcohol compound from the 2-pyridylsilanes.

2. Description of Related Art

In recent years solution(liquid) phase synthesis has been drawing attention since it appears to be superior to solid phase synthesis in that the former has versatile reactivity and scalability in addition to the advantages of cost and facile analysis. Solution phase synthesis, for example, solution phase combinatorial synthesis, however, has problems in that it requires a complicated separating method and a purifying method which are suitably designed for a product.

SUMMARY OF THE INVENTION

An object of the invention is to provide a 2-pyridylsilyl group, as a suitable auxiliary group, a phase tag, that facilitates liquid—liquid extraction for separation and purification of a compound introduced with such a group in a chemical process or sequential processes, particularly in solution phase combinatorial synthesis.

Another object of the invention is to provide a compound introduced with such a group that are useful in solution phase synthesis.

Further objects of the invention are to provide a process for introducing a 2-pyridylsilane group, as an auxiliary group, into a compound that will undergo desired chemical modifications or transformations, and a process for eliminating the introduced group after desired modifications or transformations, alternatively, a process for producing an alcohol compound that has desirably modified or transformed.

The present invention provides:

1. a 2-pyridylsilane of formula (1):

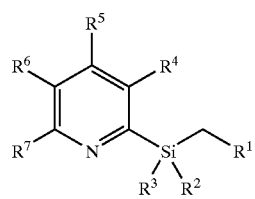

(1)

wherein $R^1$ represents an alkyl group, an aralkyl group, an alkenyl group, an alkynyl group or a trisubstituted silyl group, $R^2$ and $R^3$ are the same or different and independently represent an alkyl group, an alkoxy group, an aryl group, an aryloxy group, an aralkyl group, an aralkyloxy group, an alkenyl group, an alkynyl group or a trisubstituted silyl group, $R^4$, $R^5$, $R^6$ and $R^7$ are the same or different and independently represent a hydrogen atom, a halogen atom, an alkyl group, an alkoxy group, an aryl group, an aryloxy group, an aralkyl group, an aralkyloxy group, an alkenyl group, an alkynyl group, a cyano group, a nitro group, a hydroxy group, an alkylsulfonyl group, an arylsulfonyl group or a trisubstituted silyl group, and the alkyl groups, alkoxy groups, aryl groups, aryloxy groups, aralkyl groups, aralkyloxy groups, alkenyl groups and alkynyl groups for $R^1$ to $R^7$ may have a substituent, provided that $R^1$ is not a vinyl group.

2. A process for producing 2-pyridylsilane of formula (1) as defined above, which comprises reacting (2-pyridylsilyl)methyllithium of formula (2):

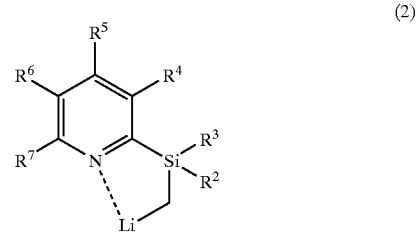

(2)

wherein $R^2$, $R^3$, $R^4$, $R^6$, $R^6$ and $R^7$ have the same meanings as defined above, with an electrophile, 3. A (2-pyridylsilyl)methyllithium of formula (2) as defined above, 4. A process for producing the 2-pyridylsilylmethyllithium of formula (2) as defined above, which comprises reacting a (2-pyridyl)methylsilane of formula (3):

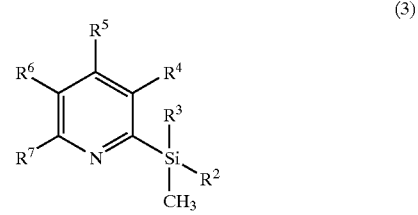

(3)

wherein $R^2$, $R^3$, $R^4$, $R^5$, $R^6$ and $R^7$ have the same meanings as defined above with a lithiating agent, 5. A process for producing an alcohol of formula (4)

(4)

wherein $R^1$ has the same meaning as defined above, which comprises reacting 2-pyridylsilane of formula (1) with a peroxide, and 6. A process for producing a 2-pyridylsilane derivative of formula (5):

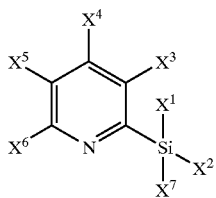

(5)

wherein $X^1$, $X^2$, $X^3$, $X^4$, $X^5$ and $X^6$ have the same meanings as defined below and $X^7$ represents an ethyl or vinyl group which may have a substituent at its 2-position, which comprises reacting a 1-alkene or a 1-alkyne, in the presence of a transition metal complex catalyst, with a 2-pyridylsilane compound of formula (6):

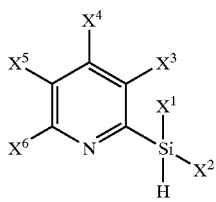

(6)

wherein $X^1$ and $X^2$ are the same or different and independently represent an alkyl group, an alkoxy group, an aryl group, an aryloxy group, an aralkyl group, an aralkyloxy group ox a trisubstituted silyl group, $X^3$, $X^4$, $X^5$ and $X^6$ are the same or different and independently represent a hydrogen atom, a halogen atom, an alkyl group, an alkoxy group, an aryl group, an aryloxy group, an aralkyl group, an aralkyloxy group, a cyano group, a nitro group, a hydroxy group, an alkylsulfonyl group, an arylsulfonyl group or a trisubstituted silyl group, provided that the allyl groups, alkoxy groups, aryl groups, aryloxy groups, aralkyl groups and aralkyloxy groups for $R^1$ to $R^7$ may have a substituent, and 7. A method for liquid—liquid phase acid/base extraction of a compound in liquid phase combinatorial synthesis, which comprises:

(a) subjecting a compound introduced with a 2-pyridylsilylmethylene group to a transformation reaction or reactions in liquid phase combinatorial synthesis to for a desirably modified or transformed compound, (b) subjecting the resulting reaction mixture containing a so transformed compound to liquid—liquid phase extraction between an organic phase and acidic aqueous phase resulting from the reaction mixture obtained in step (a) and an acidic aqueous solution and optionally an organic hydrophobic solvent to obtain an acidic aqueous phase containing the transformed compound by phase separation, and (c) liberating the transformed compound in the separated acidic aqueous phase by adding an alkali and extracting the liberated compound with an organic hydrophobic solvent to obtain an organic phase containing the liberated transformed compound by phase separation.

DESCRIPTION OF THE PREFERRED EMBODIMENT 2-pyridylsilane of formula (1) ;will be explained first.

Examples of the alkyl groups for $R^1$, $R^2$, $R^3$, $R^4$, $R^5$, $R^6$ and $R^7$ in formula (1) include a linear, branched or cyclic alkyl group having 1 to 12 carbon atoms, such as a methyl group, an ethyl group, a n-propyl group, an isopropyl group, a n-butyl group, a sec-butyl group, a t-butyl group, a n-amyl group, a neopentyl group, a n-hexyl group, a cyclohexyl group, a n-octyl group, a n-nonyl group, a menthyl group, a 2,3,4-trimethyl-3-pentyl group and a 2,4-dimethyl-3-pentyl group.

The said alkyl group may be substituted with a group selected from:

an alkoxy group having 1 to 12 carbon atoms, such as a methoxy group, an ethoxy group, a n-propoxy group, a t-butoxy group and a 1-methylheptyloxy group, a halogen atom such as a fluorine atom, a chlorine atom, a bromine atom and an iodine atom, an alkoxycarbonyl group having 2 to 8 carbon atoms such as a methoxycarbonyl group, an ethoxycarbonyl group and a t-butoxycarbonyl group, an aralkyloxycarbonyl group such as a benzyloxycarbonyl group, an aryloxycarbonyl group such as a phenoxycarbonyl group, a cyano group, a nitro group, a hydroxy group and the like.

Specific examples of the alkyl group which may be substituted with such a substituent include, for example, a 3-chloropropyl group and a 1-hydroxycyclohexyl group.

Examples of the aralkyl group for $R^1$, $R^2$, $R^3$, $R^4$, $R^5$, $R^6$ and $R^7$ in formula (1) include an $(C_1$–$C_{12})$alkyl group substituted with at least one $(C_6$–$C_{10})$aryl group (eg., a phenyl group and a naphthyl group), and specific examples thereof include, for example, a benzyl group, a 1-phenylethyl group, a 2-phenylethyl group, a 3-phenylpropyl group, a 2-naphthylethyl group, a diphenylmethyl group and the like.

The aralkyl group may be substituted with at least one group selected from the alkyl, alkoxy, alkoxycarbonyl, aralkyloxycarbonyl, aryloxycarbonyl, cyano, nitro, hydroxy group, a halogen atom or the like as described above. Specific examples of the aralkyl group having such a substituent include, for example, an α-hydroxybenzyl group, a 1-hydroxy-3-phenylpropyl group and a 1-hydroxy-1-phenylethyl group.

Examples of the alkenyl groups for $R^1$, $R^2$, $R^3$, $R^4$, $R^5$, $R^6$ and $R^7$ in formula (1) include an alkenyl group having 3 to 20 carbon atoms such as a 2-propenyl group, a 2-methyl-2-propenyl group, a 2-butenyl group, a β-styryl group, a 3-phenyl-2-propenyl group.

Examples of the alkynyl groups; for $R^1$, $R^2$, $R^3$, $R^4$, $R^5$, $R^6$ and $R^7$ in formula (1) include an alkynyl group having from 2 to 12 carbon atoms such as a 2-propynyl group, a 2-methyl-3-propynyl group and a 3-butynyl group These alkenyl and alkynyl groups may be substituted with a group selected from the foregoing alkyl group, alkoxy group, halogen atom, alkyloxycarbonyl group, cyano group, nitro group, hydroxy group, aryl group and the like.

Examples of the alkoxy groups for $R^2$, $R^3$, $R^4$, $R^5$, $R^6$ and $R^7$ in formula (1) include the same ones as listed above, wherein the alkyl moiety in the alkoxy group has the same meaning as defined for the allyl group for $R^1$ above.

In the aryl group and the aryloxy group for $R^2$, $R^3$, $R^4$, $R^5$, $R^6$ and $R^7$, the aryl group are those as described above (for example, a phenyl group and a naphthyl group and a phenoxy group). The aryl in the aryl and aryloxy group may be substituted with the same substituent group as described for the substituent, group on alkyl group in $R^1$.

In the aralkyloxy groups for $R^2$, $R^3$, $R^4$, $R^5$, $R^6$ and $R^7$, the aralkyl means the same as defined above, and specific examples of the aralkyloxy group include, for example, a benzyloxy group.

Examples of the alkylsulfonyl group for $R^4$, $R^5$, $R^6$ and $R^7$ include an alkylsulfonyl group having from 1 to 6 carbon atoms, such as a methylsulfonyl group and an ethylsulfonyl group.

Examples of the arylsulfonyl group for $R^4$, $R^5$, $R^6$ and $R^7$ include a phenylsulfonyl group and a p-tolylsulfonyl group.

The trisubstituted silyl group includes a trisubstituted silyl group that is substituted with three groups selected from the alkyl, alkoxy aryl, aryloxy group as described above and 2-pyridyl group.

Examples of the trisubstituted silyl group for $R^4$, $R^5$, $R^6$ and $R^7$ include, for example, a trimethylsilyl group, a triethylsilyl group, a t-butyldimethylsilyl group, a dimethylphenylsilyl group, a diphenylmethylsilyl group, a trimethoxysilyl group, a triphenoxysilyl group and a dimethyl (2-pyridyl)silyl group.

Specific examples of 2-pyridylsilane of formula (1) include, for example: dimethyl(n-propyl)(2-pyridyl)silane, dimethyl(n-butyl)(2-pyridyl)silane, dimethyl(n-pentyl)(2-pyridyl)silane, diethyl(n-hexyl)(2-pyridyl)silane, dimethyl (n-heptyl)(2-pyridyl)silane, dimethyl(n-octyl1)(2-pyridyl) silane; dimethyl(n-nonyl)(2-pyridyl)silane, dimethyl(2-cyclohexylethyl)(2-pyridyl)silane, dimethyl(2-cyclopropylethyl)(2-pyridyl)silane, dimethyl(4-cyanobutyl) (2-pyridyl)silane, dimethyl(3-methylbutyl)(2-pyridyl) silane, dimethyl(3-methylpentyl)(2-pyridyl)silane, dimethyl (4-methyl-pentyl)(2-pyridyl)silane, dimethyl(3,3-dimethylbutyl)(2-pyridyl)silane, dimethyl(3-ethylpentyl)(2-pyridyl)silane, dimethyl(3-ethylheptyl)(2-pyridyl)silane, dimethyl(4-chlorobutyl)(2-pyridyl)silane, dimethyl(3-butenyl)(2-pyridyl)silane, dimethyl(4pentenyl)(2-pyridyl) silane, dimethyl(4methyl3-pentenyl)(2-pyridyl)silane, dimethyl(3-butynyl)(2-pyridyl)silane, dimethyl(4-pentynyl) (2-pyridyl)silane, dimethyl(3,3-dimethoxypropyl)(2-pyridyl)silane, dimethyl(4,4-dimethoxybutyl)(2-pyridyl) silane, dimethyl(3-methoxypropyl)(2-pyridyl)silane, dimethyl(3-phenoxypropyl)(2-pyridyl)silane, dimethyl(1-hydroxycyclohexylmethyl)(2-pyridyl)silane, dimethyl(2-hydroxypropyl)(2-pyridyl)silane, dimethyl(2-hydroxypentyl)(.2-pyridyl)silane, diethyl(2-hydroxy-2-methoxypropyl)-(2-pyridyl)silane, dimethyl(2-phenylethyl) (2-pyridyl)silane, dimethyl(2-hydroxy-2-(4-fluorophenyl) ethyl)(2-pyridyl)silane, dimethyl(3-phenylpropyl)(2-pyridyl)silane, dimethyl(2-hydroxy-2-phenylethyl1)(2-pyridyl)silane, dimethyl(2-hydroxy-2-phenylpropyl)(2-pyridyl)silane, dimethyl(2-hydroxy-4-phenylbutyl)(pyridyl) silane, dimethyl(2-(2-methylphenyl)ethyl)(2-pyridyl)silane, dimethyl(2-pyridyl)(trimethylsilylmethyl)silane, dimethyl (2-pyridyl)(dimethyl(2-pyridyl)silylmethyl)silane, dimethyl (3-butenyl)(5-methyl-2-pyridyl)silane, dimethyl(3-butenyl) (6-methyl-2-pyridyl)silane, dimethyl(2-phenylethyl)(4-t-butyl-2-pyridyl)silane, dimethyl(2-phenylethyl)(4-phenyl-2-pyridyl)silane, dimethyl(4-chlorobutyl)(4-methoxy-2-pyridyl)silane, dimethyl(4-chlorobutyl)(3-fluoro-2-pyridyl) silane, dimethyl(3-butenyl)(4-cyano-2-pyridyl)silane, and dimethyl(4-phenylsulfonyl-2-pyridyl)silane.

In addition to those mentioned above, the 2-pyridylsilane of the present invention include the following compound of formula (1):

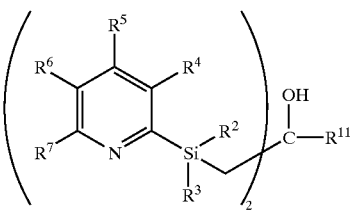

wherein $R^2$ to $R^7$ are the same as defined in formula (1), and $R^{11}$—COH is a group having a tertiary carbinol group of formula C—OH in place of a primary carbon atom in $R^1$ as defined above in formula (1)

Next, a process of the production of such a 2-pyridylsilane will be described.

The 2-pyridylsilane can be prepared by a process which comprises reacting a (2-pyridylsilyl)methyllithium. of formula (2) defined above, with an electrophile.

The reaction may be carried out by mixing (2-pyridylsilyl)methyllithium of formula (2) and the electrophile. Although the mixing order is not restricted, it is preferable, from the viewpoint of operation, that the electrophile is usually added to the (2-pyridylsilyl) methyllithium.

In formula (2) representing (2-pyridylsilyl)methyllithium, the dotted line linking the pyridine ring nitrogen and the lithium means that the lone pair of the pyridine ring nitrogen is in coordination to the lithium.

Examples of the (2-pyridyl)methyllithium of formula (2) include: [dimethyl(2-pyridyl)silyl]methyllithium, [dimethyl (5-methyl-2-pyridyl)silyl]methyllithium, [dimethyl(6-methyl-2-pyridyl)silyl]methyllithium, [dimethyl(4-t-butyl-2-pyridyl)silyl]methyllithium, [dimethyl(4-phenyl-2-pyridyl)silyl]methyllithium, [dimethyl[6-(3-butenyl)-2-pyridyl]silyl]methyllithium, [dimethyl(4methoxy-2-pyridyl) silyl]methyllithium, [dimethyl[6-(1-methylheptyl)oxy-2-pyridyl]silyl]methyllithium, [dimethyl(3-benzyloxy-2-pyridyl)silyl]methyllithium, [dimethyl(3-fluoro-2-pyridyl) silyl]methyllithium, [dimethyl(4cyano-2-pyridyl)silyl] methyllithium, [dimethyl(4-phenylsulfonyl-2-pyridyl)silyl] methyllithium and [dimethyl[6-(1,3-dioxolan-2-yl)-2-pyridyl]silyl]methyllithium.

The electrophile is not particularly limited as long as it is capable of reacting with alkyllithium compounds.

Examples of the electrophile include:

the following halide compound of formula: $R^1$–$L^1$, wherein $R^1$ has the same meaning as defined in formula (1) and $L^1$ is a halogen atom, an aldehyde compound or a ketone compound which has a carbonyl group in place of a primary or secondary carbon atom bonded to the group $L^1$ in $R^1$ as defined above, and an ester compound which has a carbonyl group in place of the primary carbon atom bonded to the group $L^1$ in $R^1$ as defined above and the carbonyl group is bonded to —$OL^2$ wherein $L^2$ has the same meaning as defined for $R^1$ in formula (1).

Specific examples of electrophile include:

a primary alkyl halide such as 1-chloroethane, 1-chloropropane, 1-chlorobutane, 1-chloropentane, 1-chlorohexane, 1-chloroheptane, 1-chlorooctane, 1-bromoethane, 1-bromopropane, 1-bromobutane, 1-bromopentane, 1-bromohexane, 1-bromoheptane, 1-bromooctane, 1-iodoethane, 1-iodopropane, 1-iodobutane, 1-iodopentane, 1-iodohexane, 1-iodoheptane, 1-iodooctane, chloromethylcyclopropane, bromomethylcyclopropane, iodomethylcyclopropane, chloromethylcyclohexane, bromomethylcyclohexane, iodomethylcyclohexane, 4chlorobutyronitrile, 4-bromobutyronitrile, 4-iodobutyronitrile, 1-chloro-2-methylpropane, 1-chloro-2-methylbutane, 1-chloro-3-methylbutane, 1-chloro-2,2-dimethylpropane, 1-chloro-2-ethylbutane, 2-ethylhexyl chloride, 1-bromo-2-methylpropane, 1-bromo-2-methylbutane, 1-bromo-3-methylbutane, 1-bromo-2,2-dimethylpropane, 1-bromo-2-ethylbutane, 2-ethylhexylbromide, 1-iodo-2-methylpropane, 1-iodo-2-methylbutane, 1-iodo-3-methylbutane, 1-iodo-2,2-dimethylpropane, 1-iodo-2-ethylbutane, 2-ethylhexyl iodide, alkenyl halide and alkyl halide both of which may be substituted, such as allyl chloride, propargyl chloride, crotyl chloride, 4-chloro-1-butene, 1-chloro-3-methylbut-2-ene, 5-chloro-1-pentene, 6-chloro-1-hexene, allyl bromide, .propargyl bromide, crotyl bromide, 4-bromo-1-butene, 1-bromo-3-methylbut-2-ene, 5-bromo-1-pentene, 6-bromo-1-hexene, allyl iodide, propargyl iodide, crotyliodide, 4-iodo-1-butene, 1-iodo-3-methylbut-2-ene, 5-iodo-pentene, 6-iodo-1-hexene, 2-chloro-1,1-dimethoxyethane, 2-chloro-1,1-diethoxyethane, 1-chloro-2,2-dimethoxypropane, 2-bromo-1,1-dimethoxyethane, 2-bromo-1,1-diethoxyethane, 1-bromo-2,2-dimethoxypropane, 2-iodo-1,1-dimethoxyethane, 2-iodo-1,1-diethoxyethane, 1-iodo-2,2-dimethoxypropane, 2-chloroethyl methyl ether, 2-chloroethyl ethyl ether, 1-chloro-2-(2-methoxyethoxy)ethane, 2-bromoethyl methyl ether, 2-bromoethyl ethyl ether, 1-bromo-2-(2-methoxyethoxy)ethane, 2-iodo-ethyl methyl ether, 2-iodo-ethyl ethyl ether, 1-iodo-2-(2-methoxyethoxy)ethane, 2-phenoxyethyl chloride, 3-phenoxypropyl chloride, 2-phenoxyethyl bromide, 3-phenoxypropyl bromide, 2-phenoxyethyl iodide, 3-phenoxypropyl iodide, benzyl chloride, pentafluorobenzyl chloride, 2-fluorobenzyl chloride, 3-fluorobenzyl chloride, 4-fluorobenzyl chloride, 2,6-difluorobenzyl chloride, (2-chloroethyl)benzene, 1-chloro-3-phenylpropane, benzyl bromide, pentafluorobenzyl bromide, 2-fluorobenzyl bromide, 3-fluorobenzyl bromide, 4fluorobenzyl bromide, 2,6-difluorobenzyl bromide, (2-bromoethyl)benzene, 1-bromo-3-phenylpropane, benzyl iodide, pentafluorobenzyl iodide, 2-fluorobenzyl iodide, 3-fluorobenzyl iodide, 4-fluorobenzyl iodide, 2,6-difluorobenzyl iodide, (2-iodoethyl)benzene, 1-iodo-3-phenylpropane, α-chloro-o-xylene, α-chloro-m-xylene, α-chloro-p-xylene, 4-(t-butyl)benzyl chloride, α-bromo-O-xylene, α-bromo-m-xylene, α-bromo-p-xylene, 4-(t-butyl)benzyl bromide, α-iodo-o-xylene, α-iodo-m-xylene, α-iodo-p-xylene, 4-(t-butyl)benzyl iodide, 1-bromo-3-chloropropane, 1-bromo-3-chloro-2-methylpropane, 1-bromo-4chlorobutane, 1-bromo-3-chlorobutane, 1-iodo-3-chloropropane, 1-iodo-4-chlorobutane and 1-iodo-3-chlorobutane;

aldehydes such as benzaldehyde, 2-fluorobenzaldehyde, 3-fluorobenzaldehyde, 4-fluorobenzaldehyde, 4-chlorobenzaldehyde, 4-bromobenzaldehyde, 2,4-difluorobenzaldehyde, 2,4dichlorobenzaldehyde, 2,4-dibromobenzaldehyde, 2-chloro-6-fluorobenzaldehyde, 2,6-dichlorobenzaldehyde, pentafluorobenzaldehyde, 3-fluoro-4-methoxybenzaldehyde, 4-methylbenzaldehyde, 2,3-dimethylbenzaldehyde, 2,4-dimethylbenzaldehyde ,4,6-trimethylbenzaldehyde, 4-methoxybenzaldehyde, 2,3-dimethoxybenzaldehyde, 2,4-dimethoxybenzaldehyde, 2,3,4-trimethoxybenzaldehyde, 2,3-dimethyl-4methoxybenzaldehyde, 4-ethoxybenzaldehyde, 4-phenoxybenzaldehyde, phenylacetaldehyde, p-tolylacetaldehyde, 3-phenylpropionaldehyde, 3-phenylbutylaldehyde, propionaldehyde, butylaldehyde, 3-methylvaleraldehyde, 3-hexenal, 3,3-dimethylbutylaldehyde, 3,5,5-trimethylhexanal and citronellal;

ketones such as cyclohexanone, acetophenone, 2'-fluoroacetophenone, 3'-fluoroacetophenone, 4'-fluoroacetophenone, 4'-chloroacetophenone, 4'-bromoacetophenone, 4'-iodoacetophenone, 4'-methylacetophenone, 4'-methoxyacetophenone, 2',3'-dimethylacetophenone, 2',4'-dimethoxyacetophenone, 4'-methylpropiophenone, 4'-methoxypropiophenone, 4'-bromopropiophenone, 2-fluorobenzophenone, 3-fluorobenzophenone, 4-fluorobenzophenone, 4-chlorobenzophenone, 4-bromobenzophenone, 4-methylbenzophenone and 4-methoxybenzophenone;

esters such as methyl acetate, ethyl acetate, t-butyl acetate, benzyl acetate, methyl crotonate, ethyl crotonate, methyl propionate, ethyl propionate, benzyl propionate and ethyl butanoate; and silanes such as chlorotrimethylsilane, trimethylsilane and dimethyl(2-pyridyl)silane.

The amount of the electrophile to be used is usually not less than 1 mol per mol of the (2-pyridylsilyl)methyllithium, and has no particular upper limit. However, since the use of too much electrophile may result in economical disadvantage, the amount of the electrophile to be used is practically not more than 5 moles, preferably not more than 2 moles. When the esters are used as electrophile, the amount of which may be a half amount as defined above per mole of the (2-pyridylsilyl)methyllithium.

The reaction of (2-pyridylsilyl)methyllithium of formula (2) with the electrophile is usually conducted in a solvent. Examples of the solvent include:

ether solvents such as diethyl ether, t-butyl methyl ether, di(n-butyl) ether and tetrahydrofuran, aliphatic hydrocarbon solvents, such as n-hexane, n-heptane and cyclohexane, aromatic hydrocarbon solvents such as benzene, toluene and xylene, and mixed solvents thereof. The amount of such a solvent to be used is not particularly limited.

The reaction temperature is usually within the range of from −150 to is 50° C., preferably within the range of from −100 to 0° C., more preferably within the range of from −100 to −50° C.

2-pyridylsilane of formula (1) thus produced can be isolated with a satisfactorily good purity, which means a substantially good purity that may not seriously hinder the subsequent process(es), by subjecting the reaction mixture, for example, to the liquid—liquid phase extraction between an organic phase and acidic or basic aqueous phase even without further column chromatography and the like.

Typical procedures are as follows. An acidic aqueous solution and, if necessary, a hydrophobic organic solvent are added to the reaction mixture and then an acidification and phase separation is performed to obtain an aqueous layer containing 2-pyridylsilane of formula (1). The aqueous layer thus obtained may be further subjected to alkali treatment and an extraction operation with a hydrophobic solvent to yield an organic layer containing 2-pyridylsilane of formula (1), which may be subjected to concentration to give the desired product.

Acidity or basicity of the aqueous phase can be optionally set by taking account of the partition of the product to be separated based on the hydrophobicity or solubility of the compound.

Examples of the acidic aqueous solution include aqueous solutions of mineral acids such as hydrochloric acid and sulfuric acid.

Examples of the hydrophobic organic solvent include:
alcohol solvents having 4 or more carbon atoms such as butanol and hexanol,
ketone solvents having 4 or more carbon atoms such as methyl ethyl ketone and methyl isobutyl ketone,
ether solvents such as diethyl ether, t-butyl methyl ether, di(n-butyl) ether and tetrahydrofuran,
ester solvents such as ethyl acetate,
aliphatic hydrocarbon solvents such as n-hexane, n-heptane and cyclohexane,
aromatic hydrocarbon solvents such as benzene, toluene and xylene,
halogenated hydrocarbon solvents such as chloroform, dichloromethane, dichloroethane and dichlorobenzene, and mixed solvents thereof.

Examples of the alibi to be used for the alkali treatment include sodium hydroxide, potassium hydroxide and potassium carbonate, which may be used as it is or in the form of an aqueous solution thereof in a subsequent process.

Next, a process for the production of (2-pyridylsilyl)methyllithium of formula (2) will be described.

The (2-pyridylsilylmethyllithium can be prepared by a process which comprises reacting a (2-pyridyl)methylsilane of formula (3) as defined above, with a lithiating agent. The resulting reaction mixture may be used directly as it is for the subsequent reaction with the aforementioned electrophile.

Examples of the (2-pyridyl)methylsilane of formula (3) include, for example:
(2-pyridyl)trimethylsilane, (5-methyl-2-pyridyl)trimethylsilane, (6-methyl-2-pyridyl)trimethylsilane, (4-t-butyl-2-pyridyl)trimethylsilane, (4-phenyl-2-pyridyl)triethylsilane, [6-(3-butenyl)-2-pyridyl]trimethylsilane, (4-methoxy-2-pyridyl)trimethylsilane, [6-(1-methylheptyl)oxy-2-pyridyl]trimethylsilane, (3-benzyloxy-2-pyridyl)trimethylsilane, (3-fluoro-2-pyridyl)trimethylsilane, (4-cyano-2-pyridyl)trimethylsilane, (4-phenylsulfonyl-2-pyridyl)trimethylsilane, and [6-(1,3-dioxolan-2-yl)-2-pyridyl]trimethylsilane.

Examples of the lithiating agent include a secondary or tertiary alkyllithium and lithium amides such as t-butyllithium, sec-butyllithium and lithium diisopropylamide. Preferably used are t-butyllithium and lithium diisopropylamide. These lithiating agents are used usually in the form of a solution in solvents described below.

The amount of the lithiating agent to be used is usually not less than 1 mol per mol of (2-pyridyl)methylsilane of formula (3), and has no particular upper limit. However, since the use of too much lithiating agent may result in economical disadvantage, the amount of the lithiating agent to be used is practically not more than 5 moles, preferably not more than 2 moles per mol of (2-pyridyl)methylsilane of formula (3).

The reaction of (2-pyridyl)methylsilane of formula (3) with the lithiating agent also is conducted usually in a solvent. The solvent may be any one in which the lithiating agent can be used. Examples of the solvent include:
ether solvents such as diethyl ether, t-butyl methyl ether, di(n-butyl) ether and tetrahydrofuran,
aliphatic hydrocarbon solvents such as n-hexane, n-heptane and cyclohexane,
aromatic hydrocarbon solvents such as benzene, toluene and xylene, and mixed solvents thereof.

The amount of the solvent to-be used is not particularly limited.

The reaction temperature is usually within the range of from −150 to 50° C., preferably within the range of from −100 to 0° C., more preferably within the range of from −100 to −50° C.

The (2-pyridyl)methylsilane of formula (3) can be prepared by known methods such as a method in which a 2-lithiopyridine is allowed to react with a chlorotrimethylsilane. The 2-lithiopyridine can be prepared by reacting a 2-halopyridine with a lithiating agent Described below is a process for the production of an alcohol from the 2-pyridylsilane of formula (1).

The 2-pyridylsilane can be easily converted into the alcohol of formula (4):

(4)

wherein $R^1$ has the same meaning as defined above with a peroxide.

Examples of the peroxide include aqueous hydrogen peroxide, peracetic acid and m-chloroperbenzoic acid, and the aqueous hydrogen peroxide is preferred from the aspect of practical utility. The amount of such a peroxide to be used is normally not less than 2 moles, preferably not less than 5 moles per mol of the 2-pyridylsilane of formula (1). The amount has no particular upper limit, but is practically not more than 50 moles per mol of the 2-pyridylsilane of formula (1).

The reaction is usually conducted in a solvent. Examples of the solvent include:
alcohol solvents such as methanol, ethanol and 2-propanol,
ether solvents such as diethyl ether, t-butyl methyl ether, di(n-butyl) ether and tetrahydrofuran,
ester solvents such as ethyl acetate,
aliphatic hydrocarbon solvents such as n-hexane, n-heptane and cyclohexane,
aromatic hydrocarbon solvents such as benzene, toluene and xylene,
halogenated hydrocarbon solvents such as chloroform, dichloromethane, dichloroethane and chlorobenzene,
aprotic polar solvents such as N,N-dimethylformamide, and mixed solvents thereof Preferred are alcohol solvents, ether solvents and mixed solvents thereof The amount of the solvent is not particularly limited.

The reaction of the 2-pyridylsilane of formula (1) with the peroxide is preferably conducted in the presence of a fluoride and/or a base.

Examples of the fluoride include:
alkali metal fluorides such as potassium hydrogenfluoride and potassium fluoride The amount of such a fluoride is usually not less than 2 moles per mol of the 2-pyridylsilane of formula (1). The amount has no particular upper limit, but is practically not more than 5 moles per mol of the 2-pyridylsilane of formula (1).

Examples of the base include inorganic bases such as potassium hydroxide, sodium hydrogencarbonate and potassium hydrogencarbonate. in The amount of the base is normally not less than 2 moles per mol of the 2-pyridylsilane of formula (1). The amount has no particular upper limit, but is practically not more than 5 moles pet mol of the 2-pyridylsilane of formula (1).

The reaction temperature is generally from −50 to 200° C., preferably from 0 to 100° C.

The alcohol of formula (4) which has been formed by the reaction of the 2-pyridylsilane of formula (1) with the peroxide can be isolated by, for example, concentrating the organic layer obtained by subjecting the reaction mass to extraction treatment, if necessary, after the addition of a hydrophobic organic solvent and water. Before isolating the alcohol of formula (4), the organic layer is preferably contacted with a reducing agent such as sodium thiosulfate to treat peroxide in case the peroxide remains in the organic layer. The alcohol isolated may be further purified by distillation, chromatography or the like, if necessary.

Examples of the alcohol cd formula (4), for example, include a carbinol substituted with above-described specific $R^1$ groups such as 2-phenylbutanol, 1-butanol, 4-phenylbutanol, 1-octanol, 4-chlorobutanol, 3-buten-l-ol, 3-propenol, 1-phenyl-1,2-ethanediol, 4-phenyl-1,2-butanediol, 1-(1-hydroxycyclohexyl)methanol and 2-phenyl-1,2-propanediol.

Thus 2-pyridylsilyl group can be introduced to a compound by the present methods, for example, using the (2-pyridylsilyl)methyllithium of formula (2) and the resulting compound such as the 2-pyridylsilane of formula (1) may be subjected to an optional chemical-reaction step(s), as long as the reaction is not affected by the presence of the 2-pyridyl group, such as alkylation (for example, methylation) and reduction step to produce a desirably modified target compound(s), and. then the obtained target compound(s) in each step and final step can be readily separated and purified from a reaction mixture by acid/base exaction due to the presence of basic pyridyl group in the modified compound molecule, and finally the introduced 2-pyridylsilyl group is readily eliminated by the present method from the desirably modified target compound(s).

The novel 2-pyridylsilane having a 2-pyridyl moiety according to the present invention can be purified by acid/base extraction, which is a liquid phase separation and purification procedure, and can be easily converted into an alcohol. It therefore is very useful as a synthetic intermediate. Thus, the 2-pyridylsilane according to the present invention can be applied for, for example, solution phase synthesis in combinatorial chemistry.

Next, a description will be made to the process for producing 2-pyridylsilane derivative of formula (5). which comprises reacting a 1-alkene or 1-alkyne in the presence of a transition metal complex catalyst with a 2-pyridylsilane compound of formula (6).

Examples of the alkyl groups for $X^1$, $X^2$, $X^3$, $X^4$, $X^5$ and $X^6$ of formula (6) include:

a linear, branched or cyclic alkyl groups having from 1 to 12 carbon atoms such as a methyl group, an ethyl group, a n-propyl group, an isopropyl group, a n-butyl group. a sec-butyl group, a t-butyl group, a n-amyl group, a neopentyl group, a n-hexyl group, a cyclohexyl group, a n-octyl group, a a-nonyl group, a menthyl group, a 2,3,4-trimethyl-3-pentyl group and a 2,4-dimethyl-3-pentyl soup.

The alkyl groups may be substituted with, for example, a group selected from:

an alkoxy group having from 1 to 12 carbon atoms such as a methoxy group, an ethoxy group, a n-propoxy- group, a t-butoxy group and a 1-methylheptyloxy group, a halogen atom such as a fluorine atom, a chlorine atom, a bromine atom and an iodine atom, an alkoxycarbonyl group having from 2 to 8 carbon atoms such as a methoxycarbonyl group, an ethoxycarbonyl group and a t-butoxycarbonyl group, an aralkyloxycarbonyl group such as a benzyloxycarbonyl group, an aryloxycarbonyl group such as a phenoxycarbonyl group, a cyano group, a nitro group or a hydroxy group.

Specific examples of the alkyl groups having such a substituent include a 3-chloropropyl group and a1-hydroxycyclohexyl group.

Examples of the aralkyl group include:

$(C_1-C_{12})$alkyl groups substituted with an $(C_6-C_{10})$aryl group(s) such as phenyl and naphthyl, e.g. a benzyl group, a 1-phenylethyl group, a 2-phenylethyl group, a 3-phenylpropyl group, a 2-naphthylethyl group and a diphenylmethyl group.

These aralkyl groups may be substituted with, for example, the foregoing alkyl group, alkoxy group, halogen atom, alkyloxycarbonyl group, cyano group, nitro group or hydroxy group.

Examples of aralkyl group having such a substituent include an α-hydroxybenzyl group, a 1-hydroxy-3-phenylpropyl group and a 1-hydroxy-1-phenylethyl group.

Examples of the alkoxy group include the same ones as described above.

Examples of the aryloxy group include ones formed of an aryl group, e.g., a phenyl group and a naphthyl group, and an oxygen atom such as a phenoxy group.

Examples of the aralkyloxy group include ones formed of the foregoing aralkyl group and an oxygen atom such as a benzyloxy group.

Examples of the alkylsulfonyl group include alkylsulfonyl groups having from 1 to 6 carbon atoms such as a methylsulfonyl group and an ethylsulfonyl group.

Examples of the arylsulfonyl group include a phenylsulfonyl group and a p-tolylsulfonyl group.

Examples of the trisubstituted silyl groups include a trimethylsilyl group, a triethylsilyl group, a t-butyldimethylsilyl group, a dimethylphenylsilyl group, a diphenylmethylsilyl group, a trimethoxysilyl group, a triphenoxysilyl group and a diethyl(2-pyridyl)silyl group.

Examples of the 2-pyridylsilane compound of formula (6) include dimethyl(2-pyridyl)silane, dimethyl(5-methyl-2 pyridyl)silane, dimethyl(6-methyl-2-pyridyl)silane, dimethyl(4t-butyl-2-pyridyl)silane, dimethyl(4phenyl-2-pyridyl)silane, dimethyl(4-methoxy-2-pyridyl)silane, dimethyl[6-(1-methylheptyl)oxy-2-pyridyl]silane, dimethyl (3-benzyloxy-2-pyridyl)silane, dimethyl(3-fluoro-2-pyridyl)silane, dimethyl(4-cyano-2-pyridyl)silane, dimethyl (4-phenylsulfonyl-2-pyridyl)silane, and dimethyl[(6-(1,3-dioxolan-2yl)-2-pyridyl]silane.

Examples of the transition metal complex catalyst include catalysts comprising a transition metal of Group 8, 9 or 10 and a ligand. Examples of Group 8 transition metal include ruthenium and the like. Examples of Group 9 transition metal include rhodium, iridium and the like Examples of Group 10 transition metal include palladium, platinum and the like.

Examples of the ligand include:

a halogen atom such as a chlorine atom, a bromine atom and an iodine atom, phosphine ligands such as triphenylphosphine, triethylphosphine and diphenylphosphinopropane, and olefin ligands such as ethylene, cyclopentadiene, pentamethylcyclopentadiene, 1,5-cyclooctadiene and norbornadiene.

Specific examples of the transition metal complex catalyst include:

a palladium complex catalyst such as tetrakis (triphenylphosphine)palladium(O) and the like, a rhodium complex catalyst such as chlorotris (triphenylphosphine)rhodium(I), cyclopentadienylbis (triphenylphosphine)rhodium(I), bis(cyclooctadiene) diiododirhodium(I) and the like, a ruthenium complex catalyst such as chloro(cyclopentadienyl)bis(triphenylphosphine)ruthenium(II), chloro(pentamethylcyclopentadienyl)1,3-bis(diphenylphosphino)propane)ruthenium(II), chloro(pentamethylcyclopentadienyl)(1,5-cyclooctadiene)ruthenium(II), dichlorotris(triphenylphosphine)ruthenium(II) and the like, an iridium complex catalyst such as chlorotris(triphenylphosphine)iridium(I), pentamethylcyclopentadienylbis(ethylene)iridium(I) and the like, a platinum complex catalyst such as (ethylene)bis(triphenylphosphine)platinum(O), trans-[chloro(ethyl)bis(triethylphosphine)platinum(II)], cis-[diethylbis(triethylphosphine)platinum(II)], dichloro(norbornadiene)platinum(II), tetrakis(triphenylphosphine)platinum(O), (cyclooctadiene)bis(triphenylphosphine)platinum(O) and the like. In view of reactivity and the like rhodium complex catalysts and platinum complex catalysts are preferred, and especially preferred are rhodium complex catalysts.

The amount of such a transition metal complex catalyst to be used is usually within the range of from 0.001 to 10 mol %, preferably within the range of from 0.01 to 5 mol % per mmol of the 2-pyridylsilane compound of formula (6).

Examples of the 1-alkene or the 1-alkyne to be reacted with the 2-pyridylsilane compound of formula (6) include the alkene and alkyne group as defined for $R^1$ of formula (1) above, wherein the alkene and alone group have a double bond or triple bond between the two end carbons of the carbon chain respectively.

Specific examples thereof include.

1-propene, 1-hexene, 1-octenemethyl acrylate, methyl 3,3diethylpentanoate-4-ene, styrene, 3-chlorostyrene, allyl phenyl ether, 2-allylphenol, vinylcyclopentane, allylcyanide, 1-pentyne, 1-octyne, 3,3-dimethyl-1-butyne, cyclopentylacetylene, phenylacetylene, 1-ethynyl-1-cyclohexanol, propargyl alcohol, methyl propionate and methyl propargyl ether.

The amount of the 1-alkene or 1-alkyne to be used is usually not less than 0.5 mol, preferably not less than 1 mol per mol of 2-pyridylsilane compound of formula (6). It has no particular upper limit, but is usually not more than 5 moles, preferably not more than 2 moles from economical aspects and the like.

The reaction of the 2-pyridylsilane compound of (6) with the 1-alkene or 1-alkyne is generally conducted an a solvent. Examples of the solvent include:

alcohol solvents such as methanol, ethanol, 1-propanol and the like, ether solvents such as diethyl ether, t-butyl methyl ether, di(n-butyl) ether, tetrahydrofuran and the like, ester solvents such as ethyl acetate and the like, aliphatic hydrocarbon solvents such as n-hexane, n-heptane, cyclohexane and the like, halogenated hydrocarbon solvents such as chloroform, dichloromethane, dichloroethane, chlorobenzene and the like, and mixed solvents thereof. The amount of such as solvent to be used has no particular limitations.

The reaction temperature is usually within the range of from 0° C. to the boiling point of a reaction mixture.

The 2-pyridylsilane derivative of formula (5) obtained according to the aforementioned process can be isolated in a good purity by subjecting the reaction mixture to the treatment mentioned below even without doing any additional separating and purifying treatment such as column chromatography and the like.

An acidic aqueous solution and, if necessary, a hydrophobic organic solvent are added to the reaction mixture to acidify the reaction mixture and separate the desired product, thereby providing the aqueous layer containing the 2-pyridylsilane derivative of formula (5). The aqueous layer is treated with alkali and subjected to extraction with a hydrophobic organic solvent to provide the organic layer containing the 2-pyridylsilane derivative of formula (5), which is subsequently concentrated.

Examples of the acidic aqueous solution include an aqueous solution of a mineral acid such as hydrochloric acid and sulfuric acid.

Examples of the hydrophobic organic solvent include alcohol solvents having 4 or more carbon atoms such butanol and hexanol, ketone solvents having 4 or more carbon atoms such as methyl ethyl ketone, methyl isobutyl ketone and the like, ether solvents such as diethyl ether, t-butyl methyl ether, di(n-butyl) ether, tetrahydrofuran and the like, ester solvents such as ethyl acetate, aliphatic hydrocarbon solvents such as n-hexane, n-heptane, cyclohexane and the like, aromatic hydrocarbon solvents such as benzene, toluene, xylene and the like, halogenated hydrocarbon solvents such as chloroform, dichloromethane, dichloroethane, chlorobenzene and the like, and mixed solvents thereof.

Examples of the alkali to be used for the alkali treatment include sodium hydroxide, potassium hydroxide and potassium carbonate, which are used as they are or in the form of an aqueous solution.

Specific examples of the 2-pyridylsilane derivative of formula (5) obtained according to the aforementioned process include:

dimethyl(1-propyl)(2-pyridyl)silane,
dimethyl(1-hexyl)(2-pyridyl)silane,
dimethyl(1-octyl)(2-pyridyl)silane,
dimethyl(2-methoxycarbonylethyl)(2-pyridyl)silane,
dimethyl(4-methoxycarbonyl-3,3,-dimethylbutyl)(2-pyridyl)silane,
dimethyl(2-phenylethyl)(2-pyridyl)silane,
dimethyl[2-(4-chlorophenyl)ethyl](2-pyridyl)silane,
dimethyl(3-phenoxypropyl)(2-pyridyl)silane,
dimethyl[3-(2-hydroxyphenyl)propyl](2-pyridyl)silane,
dimethyl(2-cyclopentylethyl)(2-pyridyl)silane,
dimethyl(3-cyanopropyl)(2-pyridyl)silane,
dimethyl(1-pentenyl)(2-pyridyl)silane,
dimethyl(1-octenyl)(2-pyridyl)silane,
dimethyl(3,3-dimethyl-1-butenyl)(2-pyridyl)silane,
dimethyl(2-cyclopentylvinyl)(2-pyridyl)silane,
dimethyl(2-phenylvinyl)(2-pyridyl)silane,
dimethyl[2-(1-hydroxycylohexyl)vinyl](2-pyridyl)silane,
dimethyl(3-hydroxy-1-propenyl)(2-pyridyl)silane,
dimethyl(2-methoxycarbonylvinyl)(2-pyridyl)silane,
dimethyl(3-methoxy-1-propenyl)(2-pyridyl)silane,
dimethyl(1-propyl)(5-methyl-2-pyridyl)silane,
dimethyl(1-hexyl)(6-methyl-2-pyridyl)silane,
dimethyl(1-octyl)(4-t-butyl-2pyridyl)silane,
dimethyl(1-octyl)(4-phenyl-2-pyridyl)silane,
dimethyl(1-octyl)(4-methoxy-2-pyridyl)silane,
dimethyl(1-octyl)(3-benzyloxy-2-pyridyl)silane,
dimethyl(1-octyl)(3-fluoro2-pyridyl)silane,
dimethyl(1-octyl)(4-cyano-2-pyridyl)silane and
dimethyl(1-octyl)(4-phenylsulfonyl-2-pyridyl)silane.

The obtained 2-pyridylsilane derivative of formula (5) is, for example, reacted with a peroxide, so that its silicon-carbon bond is cloven and it can easily be converted into an alcohol. In addition, when $X^7$ in the of formula (5) is a vinyl group which may have a substituent at its 2-position, an aldehyde, which is resulted from the isomerization from an alcohol to its more stable structure, can be obtained.

Furthermore, according to the process of the present invention is produced a 2-pyridylsilane derivative, which can be subjected to other reactions such as alkylation, e.g. methylation, reduction, and the like. The reaction products obtained can be readily separated and purified by subjecting the reaction mixtures to liquid—liquid phase acid/base extraction.

Said liquid—liquid phase acid/base extraction for separation or purification is conducted, for example, by the following method, which comprises:

(a) subjecting a compound introduced with a 2-pyridylsilylmethylene group such as a lithiated compound of formula (2) and the like, to a transformation reaction or reactions in liquid phase combinatorial synthesis to form a desirably modified or transformed compound, (b) subjecting the resulting reaction mixture containing a so transformed compound to liquid—liquid phase extraction between an organic phase and acidic aqueous phase resulting from the reaction mixture obtained in step (a) and an acidic aqueous solution and optionally an organic hydrophobic solvent to obtain an acidic aqueous phase containing the transformed compound by phase separation, and (c) liberating the transformed compound in the separated acidic aqueous phase by adding an alkali and extracting the liberated compound with an organic hydrophobic solvent to obtain an organic phase containing the liberated transformed compound by phase separation.

Additionally, the method may be optionally followed by the steps of: (1) removing the hydrophobic organic solvent from the organic phase obtained in step (c) to obtain transformed compound, and/or (2) desilylating the 2-pyridylsilyl group from the transformed compound to obtain a desirably transformed compound.

According to the present invention, 2-pyridylsilane derivatives, which can be purified or separated, namely, by the acid/base extraction, can readily be produced. The production process of the present invention can be applied, for example, to liquid phase, combinatorial synthesis in which an automated synthetic reaction(s) are conducted in a liquid phase.

The present invention will be explained further in detail below by Examples. However, it is not to be construed to limit the present invention thereto. The following Examples were conducted under an argon atmosphere.

EXAMPLE 1

After dissolving 151 mg (1.0 mmol) of (2-pyridyl) trimethylsilane in 2 ml of dry diethyl ether, 0.67 ml (1.1 mmol) of a t-butyllithium/pentane solution (the concentration: 1.64 M) was added dropwise at an inner temperature of −78° C., whereby the reaction solution turned orange indicating the formation of [dimethyl(2-pyridyl)silyl] methyllithium. After that, the mixture was continued to be stirred at an inner temperature of −78° C. for 30 minutes, and then 130 mg (1.2 mmol) of chlorotrimethylsilane was added to the mixture, which was subsequently stirred at an inner temperature of −78° C. overnight. To the resulting reaction solution was added 5 ml of 1N hydrochloric acid, and the mixture was separated to the organic and aqueous layers. The organic layer was extracted with four portions of 5 ml of 1N hydrochloric acid. The resulting aqueous layers were combined together, and neutralized by the addition of sodium hydroxide pellets. The neutralized aqueous layer was extracted with three portions of 10 ml of diethyl ether. The resulting organic layers were combined together and dried over magnesium sulfate. The solvent was evaporated to give 208 mg of dimethyl(2-pyridyl)(trimethylsilylmethyl) silane (yield: 93%; NMR purity: 95% or more).

$^1$H-NMR (CDCl$_3$, 300 MHz): δ/ppm −0.05 (s, 9H), 0.07 (s, 2H), 0.33 (s, 6H), 7.14 (ddd, J=7.5, 5.1, 1.5 Hz, 1H), 7.48 (ddd, J=7.5, 1.5, 1.2 Hz, 1H), 7.54 (td, J=7.5, 1.8 Hz, 1H), 8.75 (ddd, J=5.1, 1.8, 1.2 Hz, 1H) $^{13}$C-NMR ((CDCl$_3$, 75 MHz): δ/ppm −1.0, 1.0, 2.1, 122.5, 128.6, 133.9, 150.1, 169.2

EXAMPLE 2

Dimethyl(3-butenyl)(2-pyridyl)silane was prepared in the same manner as Example 1 except for using allyl bromide in place of chlorotrimethylsilane in Example 1. Yield: 95%
$^1$H-NMR (CDCl$_3$, 300 MHz): δ/ppm 0.29 (s, 6H), 0.86–0.94 (m, 2H), 2.00–2.12 (m, 2H), 4.83 (ddd, J=10.2, 4.8, 1.51 Hz. 1H), 4.94 (ddd, J=17.1, 3.6, 1.5 Hz, 1H), 5.82 (ddd, J=17.1, 10.2, 6.3 Hz, 1H). 7.13 (ddd, J=7.5, 4.8, 1.5 Hz, 1H, 7.45 (ddd, J=7.5, 1.5, 1.2 Hz, 1H), 7.53 (td, J7.5, 1.8 Hz, 1H), 8.74 (dd., J=4.8, 1.8, 1.2 Hz, 1H) $^{13}$C-NMR (CDCl$_3$, 75 MHz): δ/ppm −3.8, 13.7, 27.7, 112.9, 122.9, 129.0, 133.9, 141.3, 150.2, 167.6

EXAMPLE 3

Dimethyl(2-phenylethyl)(2-pyridyl)silane was prepared in the same manner as Example 1 except for using benzyl bromide in place of chlorotrimethylsilane in Example 1. Yield: 99%

$^1$H-NMR (CDCl$_3$, 300 MHz): δ/ppm 0.36 (s, 6H), 1.20–1.27(m, 2H), 2.66–2.74 (m, 2H), 7.10–7.35 (m, 6H, 7.50 (ddd, J=7.5, 1.5, 1.2 Hz, 1H), 7.58 (td, J=7.5, 1.5 Hz, 1H), 8.81 (ddd, J=4.8, 1.5, 1.2 Hz, 1H) $^{13}$C-NMR (CDCl$_3$, 75 MHz): δ/ppm −3.9, 16.7, 29.7, 122.7, 125.5, 127.8, 128.3, 129.1, 133.9, 144.9, 150.2, 167.4

EXAMPLE 4

Dimethyl(4-phenylbutyl)(2-pyridyl)silane was prepared in the same manner as Example 1 except for using 1-bromo-3-phenylpropane in place of chlorotrimethylsilane in Example 1. Yield: 84%

$^1$H-NMR (CDCl$_3$, 300 MHz): δ/ppm 0.33 (s, 6H) 0.86–0.94 (m, 2H) 1.36–1.49 (m, 2H) 1.60–1.72 (m, 2H) 2.60 (t, J=7.8 Hz, 1H) 7.13–7.22 (m, 4H) 7.23–7.30 (m, 2H) 7.49 (ddd, J=7.5, 1.5. 1.2 Hz, 1H) 7.57 (td, J=7.5, 1.8 Hz, 1H) 8.80 (ddd, J=4.5, 1.8, 1.2 Hz, 1H) $^{13}$C-NMR (CDCl$_3$, 75 MHz): δ/ppm −3.8, 14.5, 23.3, 35.1, 35.4, 122.7, 125.5, 128.2, 128.4, 129.1, 133.9, 142.8, 150.2, 167.9

EXAMPLE 5

Dimethyl(4-chlorobutyl)(2-pyridyl)silane was prepared in the same manner as Example 1 except for using 1-bromo-3-chloropropane in place of chlorotrimethylsilane in Example 1. Yield: 86%

$^1$H-NMR (CDCl$_3$, 300 MHz): δ/ppm 0.29 (s, 6H), 0.77–0.84 (m, 2H), 1.39–1.51 (m, 2H), 1.69–1.80 (m, 2H), 3.47 (t, J=6.6 Hz, 2H), 7.15 (ddd, J=7.5, 4.8, 1.8 Hz, 1H), 7.45 (ddd, J=7.6, 1.8, 1.2 Hz, 1Hz), 7.54 (td, J=7.6, 1.8 Hz, 1H), 8.74 (ddd, J=4.8, 1.8, 1.2 Hz, 1H) $^{13}$C-NMR (CDCl$_3$, 75 MHz): δ/ppm −3.9. 13.8, 20.9, 35.8, 44.5, 122.7, 129.0, 133.9, 150.2, 167.4

EXAMPLE 6

After dissolving 151 mg (1.0 mmol) of (2-pyridyl) trimethylsilane in 2 ml of dry diethyl ether, 0.67 ml (1.1 mmol) of a t-butyllithium/pentane solution (the concentration: 1.64 M) was added dropwise thereto at an inner temperature of −78° C., whereby the reaction solution tuned orange indicating the formation of [dimethyl(2-pyridyl)silyl]methyllithium. After that, the mixture was continued to be stirred at an inner temperature of −78° C. for 30 minutes, and then 127 mg (1.2 mmol) of benzaldehyde was added to the mixture, which was subsequently stirred at an inner temperature of −78° C. for 1 hour. The mixture was further stirred at 0° C. for 3 hours. To the resulting reaction solution was added 5 ml of a saturated aqueous ammonium chloride solution. The mixture was neutralized with a saturated aqueous sodium hydrogencarbonate solution.

The neutralized aqueous layer was subjected to extraction. The resulting organic layer was dried over magnesium sulfate and the solvent was evaporated. The resulting concentrated residue was further purified with silica gel chromatography to give dimethyl(2-hydroxy-2-phenylethyl)(2-pyridyl)silane. Yield: 85%

$^1$H-NMR (CDCl$_3$, 300 MHz): δ/ppm 0.27 (s, 3H), 0.38 (s, 3H), 1.39 (dd, J=14.7, 3.3 Hz, 1H), 1.57 (dd, J=14.7, 10.2 Hz, 1H), 5.05 (dd, J=10.2, 3.3 Hz, 1H), 7.16 −7.26 (m, 2H), 7.31 ((t, J=7.8 Hz, 2H), 7.44 (d, J=7.8 Hz, 2H), 7.54 (dm, J=7.8 Hz, 1H), 7.63 (tm, J=7.8 Hz, 1H), 8.70 (dm, J=5.1 Hz, 1H) $^{13}$C-NMR (CDCl$_3$, 75 MHz): δ/ppm −3.0, −2.7, 28.1, 70.0, 123.1, 125.2, 126.4, 128.0, 129.3, 135.0, 148.0, 148.9, 166.5

EXAMPLE 7

Dimethyl(4-phenyl-2-hydroxybutyl)(2-pyridyl)silane was prepared in the same manner as Example 6 except for using 3-phenylpropylaldehyde in place of benzaldehyde in Example 6. Yield: 63%

$^1$H-NMR (CDCl$_3$, 300 MHz): δ/ppm 0.32 (s, 3H), 0.38 (s, 8H), 1.12 (ddd, J=15.0, 3.0, 0.9 Hz, 1H), 1.24 (dd, J15.0, 10.2 Hz, 1H), 1.72–2.00 (m, 2H), 2.73 (ddd, J=13.5, 10.5, 6.0 Hz, 1H), 2.89 (ddd, J=13.5, 10.5, 5.7 Hz, 1H), 3.93–4.04 (m, 1H), 7.13–7.32 (m, 6H), 7.55 (ddd, J=7.5, 2.4, 0.9 Hz, 1H), 7.64 (tdd, J=7.5, 1.5, 0.9 Hz, 1H), 8.09 (dm, J=4.8 Hz, 1H) $^{13}$C-NMR (CDCl$_3$, 75 MHz): δppm −2.9, −2.2, 25.2, 32.5, 43.0, 67.1, 123.2, 125.6, 128.2, 128.5, 129.4, 135.0, 1.42, 142.9, 166.8

EXAMPLE 8

Dimethyl(1-hydroxycyclohexylmethyl)(2-pyridyl)silane was prepared in the same manner as Example 6 except for using cyclohexanone in place of benzaldehyde in Example 6. Yield: 64%

$^1$H-NMR (CDCl$_3$, 300 MHz): δ/ppm 0.3 (s, 6H), 1.18–1.50 (m, 6H), 1.30 (s, 2H), 1.55–1.72 (m, 4H), 6.53 (brs, 1H), 7.18 (ddd, J=7.2, 5,1 1.5 Hz, 1H), 7.51 (ddd, J=7.8, 1.5, 1.2 Hz, 1H), 7.60 (ddd, J=7.8, 7.2, 1.8 Hz, 1H), 8.64 (ddd, J=5.1, 1.8, 1.2 Hz, 1H) $^{13}$C-NMR (CDCl$_3$, 75 MHz): δ/ppm −0.5, 22.8, 25.6, 31.2, 41.4, 70.3, 123.0, 129.5, 134.9, 148.9, 167.6

EXAMPLE 9

Dimethyl(2-hydroxy-2-phenylpropyl)(2-pyridyl)silane was prepared in the same manner as Example 6 except for using acetophenone in place of benzaldehyde in Example 6. Yield: 55%

$^1$H-NMR (CDCl$_3$, 300 MHz): δ/ppm −0.26 (s, 3H), 0.28 (s, 3H), 1.64 (s, 3H), 1.76 (s, 2H), 7.10–7.23 (m, 2H), 7.26 (tm, J=7.2 Hz, 2H), 7.43 (dm, J=7.8 Hz, 1H), 7.53 (dm, J=7.2 Hz, 2H), 7.59 (tdm, J=7.8, 1.5 Hz, 1H), 7.89 (brs, 1H), 8.70 (dm, J=5.1 Hz, 1H) $^{13}$C-NMR (CDCl$_3$, 75 MHz): δ/ppm −2.2, −1.2, 33.8, 35.0, 72.6, 123.1, 124.7, 125.8, 127.8, 129.4, 135.0, 148.6, 151.1, 167.1

EXAMPLE 10

Dimethyl(2-pyridyl)[dimethyl(2-pyridyl)silylmethyl]silane was prepared in the same manner as Example 6 except for using dimethyl(2-pyridyl)silane in place of benzaldehyde in Example 6. Yield: 63%

$^1$H-NMR (CDCl$_3$, 300 MHz): δ/ppm 0.22 (s, 12H), 0.38 (s, 2H), 7.08 (ddd, J=7.5, 4.8, 1.5 Hz, 2H), 7.38 (ddd, J=7.5, 1.5, 1.2 Hz, 2H), 7.46 (td, J=7.5, 1.8 Hz, 2H), 8.68 (ddd, J=4.8, 1.8, 1.2 Hz, 2H) $^{13}$C-NMR (CDCl$_3$, 75 MHz): δ/ppm −1.2, 0.1, 122.5, 128.6, 133.8, 150.0, 168.7

EXAMPLE 11

To 129 mg (0.5 mmol) of the (2-hydroxy-2-phenylethyl)(2-pyridyl)silane obtained in Example 6, a solution of 58 mg (1.0 mmol) of potassium fluoride and 100 mg(1.0 mmol) of potassium hydrogencarbonate in methanol(1 ml)tetrahydrofuran(1 ml) was added, followed by 1.71 g (15 mmol) of 30% aqueous hydrogen peroxide. The mixture was continued to be stirred at an inner temperature of 50° C. for 6 hours, and then cooled to room temperature. After addition of 10 ml of water, the mixture was extracted with four portions of 10 ml of diethyl ether. The separated organic layers were combined together and washed with 10 ml of a 15% aqueous sodium thiosulfate solution. After drying over magnesium sulfate, the residue after the evaporation of the solvent was purified with silica gel chromatograph to give 66 mg of phenyl-1,2-ethanediol. Yield: 96%

EXAMPLE 12

4-Phenylbutanol was prepared in the same manner as Example 11 except for using, in Example 11, the dimethyl (4-phenylbutyl)(2-pyridyl)silane obtained in Example 4 in place of the (2-hydroxy-2-phenylethyl)(2-pyridyl)silane obtained in Example 6. Yield: 98%

EXAMPLE 13

4-Phenyl-1,2-butanediol was prepared in the same manner as Example 1 except for using, in Example 11, the dimethyl(4-phenyl-2-hydroxybutyl)(2-pyridyl)silane obtained in Example 7 in place of the (2-hydroxy-2-phenylethyl)(2-pyridyl)silane obtained in Example 6. Yield: 90%

EXAMPLE 14

(1-Hydroxycyclohexyl)methanol was prepared in the same manner as Example 11 except for using, in Example 11, the (1-hydroxycyclohexylmethyl)(2-pyridyl)silane obtained in Example 8 in place of the (2-hydroxy-2-phenylethyl)(2-pyridyl)silane obtained in Example 6. Yield: 95%

EXAMPLE 15

2-Phenyl-1,2-propanediol was prepared in the same manner as Example 11 except for using, in Example 11, the dimethyl(2-hydroxy-2-phenylpropyl)(2-pyridyl)silane obtained in Example 9 in place of the (2-hydroxy-2-phenylethyl)(2-pyridyl)silane obtained in Example 6. Yield: 93%

EXAMPLE 16

The same procedures as Example 1 were repeated except for conducting the reaction between (2-pyridyl)

trimethylsilane and t-butyllithium using diethyl ether-$d_{10}$ in place of dry diethyl ether. The resulting solution was subjected to $^1$H-NMR measurement. According to the comparison with the $^1$H-NMR measurement of the starting (2-pyridyl)trimethylsilane, the chemical shift assigned to the hydrogen atom on the pyridine ring had changed and there was coordination of the pyridine ring nitrogen atom to lithium. The measurements are shown in the following table.

TABLE 1

|  | Dimethyl(2-pyridyl)-methyllithium | Starting (2-pyridyl)-trimethylsilane |
| --- | --- | --- |
| 3-Hydrogen | 7.60 | 7.44 |
| 4-Hydrogen | 7.72 | 7.52 |
| 5-Hydrogen | 7.33 | 7.12 |
| 6-Hydrogen | 8.61 | 8.68 |

(Unit: δ/ppm)

COMPARATIVE EXAMPLE 1

The procedures were repeated in the same manner as Example 1 except for using (3-pyridyl)trimethylsilane in place of (2-pyridyl)trimethylsilane in Example 1. There was no formation of dimethyl(3-pyridyl)silylmethyllithium, however.

COMPARATIVE EXAMPLE 2

The procedures were repeated in the same manner as Example 1 except for using phenyltrimethylsilane in place of (2-pyridyl)trimethylsilane in Example 1. There was no formation of dimethylphenylsilylmethyllithium, however.

EXAMPLE 17

In 0.6 ml of acetonitrile were dissolved 166 mg (1.5 mmol) of 1-octene and 23 mg (0.25 μmol) of chlorotris(triphenylphosphine)rhodium(I). To this solution was added dropwise 69 mg (0.5 mmol) of dimethyl(2-pyridyl)silane at room temperature over 1 hour.

After the completion of the addition, the solution was continued to be stirred for 30 mutes at room temperature, followed by the addition of 6 ml of 1N hydrochloric acid and 5 ml of diethyl ether. After stirring for another 30 minutes, the solution was separated into the organic and aqueous layers. The organic layer was extracted with five portions of 6 ml of 1N hydrochloric acid, and the resulting aqueous layers were combined together and turned basic with the addition of sodium hydroxide pellets. The aqueous layer was extracted with three portions of 10 ml of diethyl ether. The resulting organic layer was dried over potassium carbonate and the solvent was evaporated under reduced pressure to give 107 mg of dimethyl(1-octyl)(2-pyridyl)silane in the form of colorless oil (Yield: 86%; the purity by NMR and GC: >95%).

$^1$H-NMR (CDCl$_3$, 500 MHz): δ/ppm 0.30 (s, 6H), 0.80–0.84 (m, 2H), 0.86 (t, J=7.1 Hz, 1H), 1.20–1.37 (m, 12H), 7.18 (ddd, J=7.7, 5.0, 1.5 Hz, 1H), 7.48 (dt, J=7.7, 1.5 Hz, 1H), 7.57 (td, J=7.7, 1.5 Hz, 1H), 7.77 (dt, J=5.0, 1.5 Hz, 1H) $^{13}$C-NMR (CDCl$_3$, 125 MHz): δ/ppm –3.6. 14.1, 14.8, 22.6, 23.7, 29.22, 29.23, 31.9, 33.5, 122.6, 129.0, 133.8, 150.1, 168.0

EXAMPLE 18

To 1.0 ml of diethyl ether were added 10 mg (0.25 μmol) of bis(cyclooctadiene)platinum, 13 mg (0.50 μmol) of triphenylphosphine and 165 mg (1.5 mmol) of 1-octyne, and 69 mg (0.5 mmol) of dimethyl(2-pyridyl)silane was added dropwise thereto at room temperature over 1 hour. Further, the mixture was continued to be stirred for 6 hours at an inner temperature of 40° C., followed by the addition of 6 ml of 1N hydrochloric acid and 5 ml of diethyl ether. After the mixture was stirred for 30 minutes, it was left stand and separated into the organic and aqueous layers. The organic layer was extracted with five portions of 6 ml of 1N hydrochloric acid, and the resulting aqueous layers were combined together and turned basic with the addition of sodium hydroxide pellets. This aqueous layer was extracted with three portions of 10 ml of diethyl ether. The resulting organic layer was dried over magnesium sulfate and the solvent was evaporated off under reduced pressure to give 112 mg of dimethyl(1-octenyl)(2-pyridyl)silane. Yield: 90%

REFERENTIAL EXAMPLE 1

After 121 mg (2.09 mmol) of potassium fluoride and 204 mg (2.04 mmol) of potassium hydrogencarbonate were dissolved in a mixed solvent of 2.5 ml of methanol and 2.5 ml of tetrahydrofuran, 246 mg (0.99 mmol) of dimethyl(1-octyl)(2-pyridyl)silane which had been prepared in the same manner as Example 17 and 3.47 g (30.4 mmol) of 30% aqueous hydrogen peroxide were added.

The solution after mixing was continued to be stirred for 12 hours at an inner temperature of 50° C. After that, the solution was cooled to room temperature. To the solution was added 20 ml of water, and the mixture was extracted with five portions of 20 ml of diethyl ether. The resulting organic layers were combined together, washed with 20 ml of 15% sodium thiosulfate and dried over sodium sulfate. The solvent was evaporated under reduced pressure to give 1-octanol (Yield: 82%).

REFERENTIAL EXAMPLE 2

In 0.2 ml of acetonitrile were dissolved 213 mg (1.5 mmol) of methyl 3,3-dimethylpentanoate-4-ene and 23 mg (0.25 μmol) of chlorotris(triphenylphosphine)rhodium(I). To this solution was added dropwise 69 mg (0.5 mmol) of dimethyl(2-pyridyl)silane at room temperature over 1 hour.

After the completion of the addition, the mixture was continued to be stirred at room temperature for 1 hour, followed by the addition of 6 ml of 1N hydrochloric acid and 2 ml of diethyl ether. After the additional 30 minutes stirring, the solution was separated into the organic and aqueous layers. The resulting organic layer was extracted two portions of 6 ml of 1N hydrochloric acid, and the resulting aqueous layers were combined together, neutralized with sodium hydroxide pellets and extracted with three portions of 10 ml of diethyl ether.

The organic layer was dried over magnesium sulfate, the solvent was then evaporated off under reduced pressure to give 116 mg of dimethyl(4-methoxycarbonyl-3,3-dimethylbutyl)(2-pyridyl)silane (Yield: 83%; the purity: >95%).

$^1$H-NMR (CDCl$_3$, 300 MHz): δ/ppm 0.24 (s, 6H), 0.66–0.74 (m, 2H), 0.87 (s, 6H), 1.20–1.30 (m, 2H), 2.11 (s, 2H), 3.52 (s, 3H), 7.11 (ddd, J=7.5, 4.8, 1.5 Hz, 1H), 7.42 (ddd, J=7.5, 1.5, 0.9 Hz, 1 Hz), 7.50 (td, J=7.6, 1.5 Hz, 1H), 8.69 (ddd, J=4.8, 1.2, 0.9 Hz, 1H) $^{13}$C-NMR (CDCl$_3$, 75 Mz): δ/ppm –4.1, 8.4, 26.6, 33.9, 35.8, 44.9, 50.9, 122.7, 129.1, 133.9, 150.2, 167.6, 173.0

To 40 mg (143 μmol) of the resulting dimethyl(4-methoxycarbonyl-3,3-dimethylbutyl)(2-pyridyl)silane was-added 1 ml of diethyl ether to form a solution. To this solution was added dropwise a methyllithium/diethyl ether solution (716 μmol) at an inner temperature of 0° C.

After the completion of the addition, the mixture was stirred at an inner temperature of 0° C. for 1 hour and 5 ml of 1N hydrochloric acid was added. Further, the mixture was continued to be stirred for 30 minutes at an inner temperature of 0° C., and then separated into the organic and aqueous layers. The resulting organic layer was turned basic with the addition of sodium hydroxide pellets and extracted with two portions of 10 ml of diethyl ether. The organic layer was dried over magnesium sulfate, and the solvent was evaporated off to give 37 mg of dimethyl(5-hydroxy-3,3-dimethylhexyl)(2-pyridyl)silane (Yield: 93%; the purity: >95%).

$^1$H-NMR (CDCl$_3$, 300 MHz): δ/ppm 0.27 (s, 6H), 0.77–0.84 (m, 2H), 0.94 (s, 6H), 1.24 (s, 6H), 1.30–1.38 (m, 2H), 1.49 (s, 2H), 2.34 (brs, 1H), 7.17 (ddd, J=7.5, 4.8, 1.5 Hz, 1H), 7.47 (ddd, J=7.5, 1.5, 1.2 Hz, 1 Hz), 7.56 (td, J=7.5, 1.8 Hz, 1H), 8.73 (ddd, J=48, 1.8, 1.2 Hz, 1H) $^{13}$C-NMR (CDCl$_3$, 75 Hz): δ/ppm −3.7, 8.3, 28.6, 31.7, 34.4, 37.1, 52.0, 72.0, 122.8, 129.2, 134.1, 150.0, 167.8

After 69 mg (1.18 mmol) of potassium fluoride and 118 mg (1.18 mmol) of potassium hydrogen carbonate were dissolved in 1 ml of methanol, to this solution were added both 2.0 g (17.7 mol) of 30% aqueous hydrogen peroxide and a solution prepared by dissolving, in 1.5 ml of tetrahydrofuran, 165 mg (590 μmol) of dimethyl(5-hydroxy-3,3-dimethylhexyl)(2-pyridyl)silane which had been prepared in the same manner as Example 17. The solution after mixing was continued to be stirred for 22 hours at an inner temperature of 50° C. After cooling to room temperature, 10 ml of water was added to the solution after the reaction, and the mixture was extracted with three portions of 20 ml of diethyl ether. The resulting organic layers were combined together, washed with 20 ml of 15% sodium thiosulfate and dried over sodium sulfate. The solvent was evaporated off under reduced pressure to give crude 2,4,4-trimethyl-2,6-hexanediol. This was purified with a silica gel column using a mixed solvent of hexane/ethyl acetate=1/1 (volume ratio) to give 94 mg of 2,4,4-trimethyl-2,6-hexanediol in the form of colorless oil (Yield: 99%; the purity: >95%).

What is claimed:

1. A method for liquid—liquid phase extraction of a compound in liquid phase combinatorial synthesis, which comprises:

(a) subjecting a compound introduced with a 2-pyridylsilylmethylene group to a transformation reaction or reactions in liquid phase combinatorial synthesis to form a desirably modified or transformed compound, (b) subjecting the resulting reaction mixture containing a so transformed compound to liquid—liquid phase extraction between an organic phase and acidic aqueous phase resulting from the reaction mixture obtained in step (a) and an acidic aqueous solution and optionally an organic hydrophobic solvent to obtain an acidic aqueous phase containing the transformed compound by phase separation, and (c) liberating the transformed compound in the separated acidic aqueous phase by adding an alkali and extracting the liberated compound with an organic hydrophobic solvent to obtain an organic phase containing the liberated transformed compound by phase separation.

2. The method according to claim 1, which further comprises the step of:

(1) removing the hydrophobic organic solvent from the organic phase obtained in step (c) to obtain transformed compound, and/or (2) desilylating the 2-pyridylslyl group from the transformed compound to obtain a desirably transformed compound.

* * * * *